United States Patent
McDowell (10) Patent No.: US 12,337,062 B2
(45) Date of Patent: Jun. 24, 2025

(54) SYSTEM AND METHOD OF ADMINISTERING A FREEZABLE COUGH DROP TO A USER

(71) Applicant: Tom McDowell, Pebble Beach, CA (US)

(72) Inventor: Tom McDowell, Pebble Beach, CA (US)

( * ) Notice: Subject to any disclaimer, the term of this patent is extended or adjusted under 35 U.S.C. 154(b) by 579 days.

(21) Appl. No.: 16/842,578

(22) Filed: Apr. 7, 2020

(65) Prior Publication Data

US 2021/0308045 A1  Oct. 7, 2021

(51) Int. Cl.
| | |
|---|---|
| *A61K 9/00* | (2006.01) |
| *A61J 1/03* | (2023.01) |
| *A61J 3/06* | (2006.01) |
| *A61K 33/30* | (2006.01) |
| *A61K 36/28* | (2006.01) |
| *A61K 36/61* | (2006.01) |
| *A61K 47/12* | (2006.01) |
| *A61K 47/24* | (2006.01) |

(52) U.S. Cl.
CPC ............. *A61K 9/0056* (2013.01); *A61J 1/035* (2013.01); *A61J 3/06* (2013.01); *A61K 33/30* (2013.01); *A61K 36/28* (2013.01); *A61K 36/61* (2013.01); *A61K 47/12* (2013.01); *A61K 47/24* (2013.01); *A61J 2200/44* (2013.01)

(58) Field of Classification Search
CPC ...... A61K 9/0056; A61K 33/30; A61K 36/28; A61K 36/61; A61K 47/12; A61K 47/24; A61K 36/42; A61J 1/035; A61J 3/06; A61J 2200/44; A61P 1/00
See application file for complete search history.

(56) References Cited

U.S. PATENT DOCUMENTS

| | | | | |
|---|---|---|---|---|
| 2006/0024335 A1* | 2/2006 | Roger | .................. | A61K 9/0056 424/400 |
| 2007/0036838 A1* | 2/2007 | Keenan | ................. | A61K 31/445 514/315 |
| 2010/0168074 A1* | 7/2010 | Culligan | .............. | B65D 75/327 514/629 |
| 2015/0208703 A1* | 7/2015 | Turner | ..................... | A23L 27/36 426/548 |
| 2015/0273009 A1* | 10/2015 | Cifter | .................... | A61K 35/644 424/756 |
| 2018/0235874 A1* | 8/2018 | Hickham | ............... | A61K 31/70 |

FOREIGN PATENT DOCUMENTS

| | | | | |
|---|---|---|---|---|
| CN | 1446900 A | * | 10/2003 | ............... C12G 3/04 |
| DE | 202005009181 U1 | * | 7/2006 | ............. A61K 36/09 |
| JP | H1036266 A | * | 2/1998 | ........... A61K 31/485 |
| WO | 2012062646 A1 | | 5/2012 | |

OTHER PUBLICATIONS

English machine translation of Nakai—JP-H1036266-A (4 pages). (Year: 1998).*
English machine translation of Yu—CN 1446900 A (3 pages). (Year: 2003).*
English machine translation of Klosterfrau—DE 20 2005 009181 U1 (6 pages). (Year: 2006).*
Kolassa, Norbert, Menthol differs from other terpenic essential oil constituents, Regulatory Toxicology and Pharmacology 65 (2013) 115-118. (Year: 2013).*
How to Treat a Cough From a Cold or the Flu, retrieved from the internet, retrieved on Feb. 11, 2025; <URL: https://symptoms.webmd.com/cold-flu-map/treating-your-cough>.
Nature's Way Zinc Lozenges with Vitamin C & Echinacea, Immune Support*, 23 mg of Zinc & 100 mg of Vitamin C per Serving, Wild Berry Flavored, 60 Lozenges (Packaging May Vary), retrieved from the internet, retrieved on Feb. 11, 2025; <URL: https://www.amazon.com/Natures-Way-Zinc-Lozenge-Lozenges/dp/B00024D3SK>.
Soothing Properties of Glycerol in Cough Syrups for Acute Cough Due to Common Cold, retrieved from the internet, retrieved on Feb. 11, 2025; <URL: https://pdfs.semanticscholar.org/bdcc/df52e93a7c958a10946474ee0c2b4db09d1b.pdf>.
Halls (cough drop), retrieved from the internet, retrieved on Feb. 11, 2025; <URL: https://en.wikipedia.org/wiki/Halls_(cough_drop)>.

* cited by examiner

*Primary Examiner* — Aradhana Sasan (57) ABSTRACT

A system and method of administering a freezable cough drop to a user. The system includes a quantity of medicated solution and a freezer. The medicated solution is an aqueous solution with medicinal and soothing properties and is portioned into a plurality of dosages. The method begins with the plurality of dosages being positioned within the freezer. At least one arbitrary dosage is removed from the freezer. Moreover, the arbitrary dosage is any one of the plurality of dosages. The arbitrary dosage is placed within a mouth of the user. The arbitrary dosage is dispensed from the mouth into a sore throat of the user by gradually dissolving the arbitrary dosage. The system further includes a blister pack with a plurality of blister compartments that houses the plurality of dosages. An arbitrary dosage is ejected out of the corresponding compartment before being placed within the mouth of the user.

9 Claims, 8 Drawing Sheets

FIG. 8

SYSTEM AND METHOD OF ADMINISTERING A FREEZABLE COUGH DROP TO A USER

FIELD OF THE INVENTION

The present invention generally relates to cough drops. More specifically, the present invention administers a freezable cough drop to a user for anesthetizing affects with a sore throat of a user.

BACKGROUND OF THE INVENTION

A sore throat is common symptom of allergies, colds, sicknesses, and viruses. Having a sore throat is enduring symptom that is makes it difficult to communicate with others, as well as eat certain foods. In order to relieve a sore throat, home remedies, such as gargling with salt water, drinking tea with honey, and drinking plenty of water, though aid in the recovery of a sore throat, only temporarily soothe the pain and annoyance of the sore throat. Consuming cough drops is an easy solution that soothes a sore throat while performing other tasks and activities. However, each cough drop provides an even shorter time period of relief and must constantly be sucked on in order to feel relief.

The present invention provides constant relief for a sore throat for an extended period of time. The method of the present invention administers a freezable cough drop to a user in order to sooth a sore throat. The freezable cough drop may be a variety of flavors that best appeal to the taste of an individuals. The flavors may include, but are not limited to, cherry grape, orange, and lemon. Moreover, each freezable cough drop may be a variety of shapes that are aesthetically pleasing. The present invention provides anesthetizing effects for a sore throat by directly applying to the sore. The cold temperature of the present invention relieves the pain of a sore throat. The present invention also includes medicinal properties that aid in the recovery of a sore throat.

DETAIL DESCRIPTIONS OF THE INVENTION

All illustrations of the drawings are for the purpose of describing selected versions of the present invention and are not intended to limit the scope of the present invention.

The present invention is a system and method of administering a freezable cough drop to a user. The present invention soothes a sore throat and aids in the healing of the sore throat. The present invention anesthetizes a sore throat and relieves the pain of the sore throat for significant amount of time. Thus, the physical system of the present invention is provided with a quantity of medicated solution and a freezer (Step A), seen in FIG. 1. The quantity of medicated solution is an aqueous solution and is portioned into a plurality of dosages. Moreover, the quantity of medicated solution coats the sore throat and has medicinal properties that are able to heal the sore throat. Each of the plurality of dosages is a measured amount of medicated solution that provides the necessary amount of medicated solution to readily sooth a sore throat. The freezer is used to freeze the plurality of dosages such that the plurality of dosages to harden and may be sucked by a user.

Figure 2:
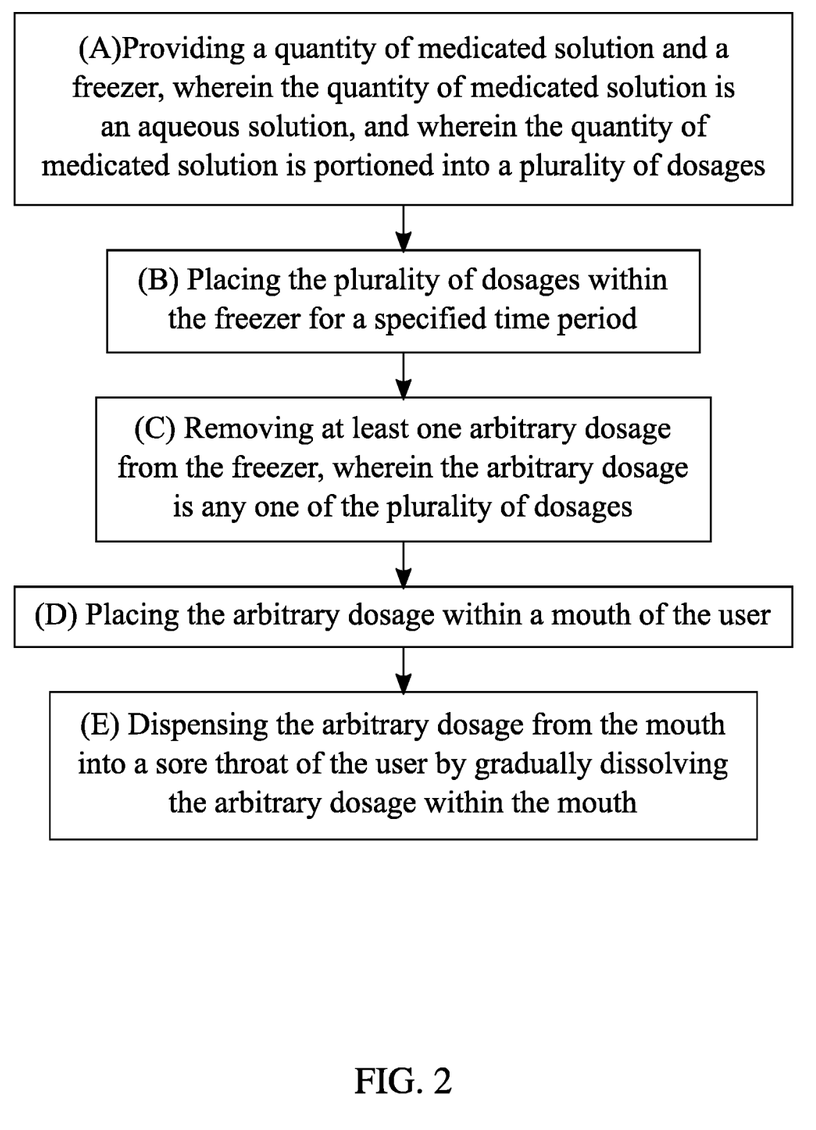
FIG. 2 is a flowchart illustrating the overall process for a method of the present invention.
Figure 3:
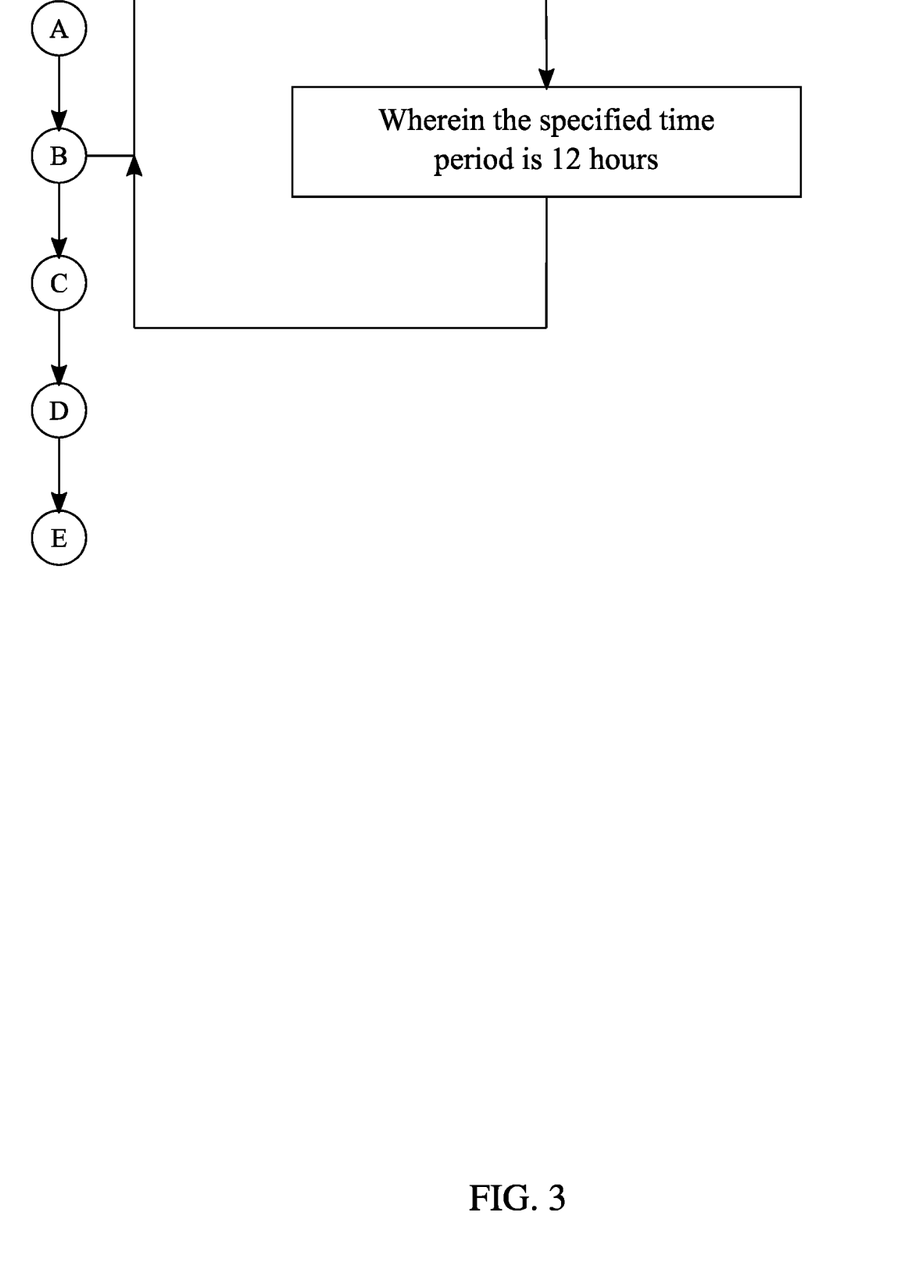
FIG. 3 is a flowchart illustrating the subprocess for the amount time required to freeze the quantity of dosages.

The overall process for the method of the present invention includes the following steps that are implemented with quantity of medicated solution and the freezer. In order for the plurality of dosages to be frozen, the plurality of dosages is placed within the freezer for a specified time period (Step B), seen in FIG. 2. The specified time period is preferably 12 hours, seen in FIG. 3. However, the specified time period may vary depending on an internal temperature of the freezer. In order to access the plurality of dosages once frozen, at least one arbitrary dosage is removed from the freezer, wherein the arbitrary dosage is any one of the plurality of dosages (Step C). The user may begin to relieve a sore throat once the arbitrary dosage is placed within a mouth of the user (Step D). The arbitrary dosage is dispensed from the mouth into the sore throat of the user by gradually dissolving the arbitrary dosage within the mouth (Step E) while sucking on the arbitrary dosage. As the arbitrary dosage dissolves, the cooling sensation of the arbitrary dosage anesthetizes the sore throat, and the medicated solution coats the sore throat. The plurality of dosages is typically ingested throughout the duration of a cold or sickness in order to continuously receive the effects of the medicated solution as Step A through Step E, shown in FIG. 2, are executed in sequence.

Figure 4:
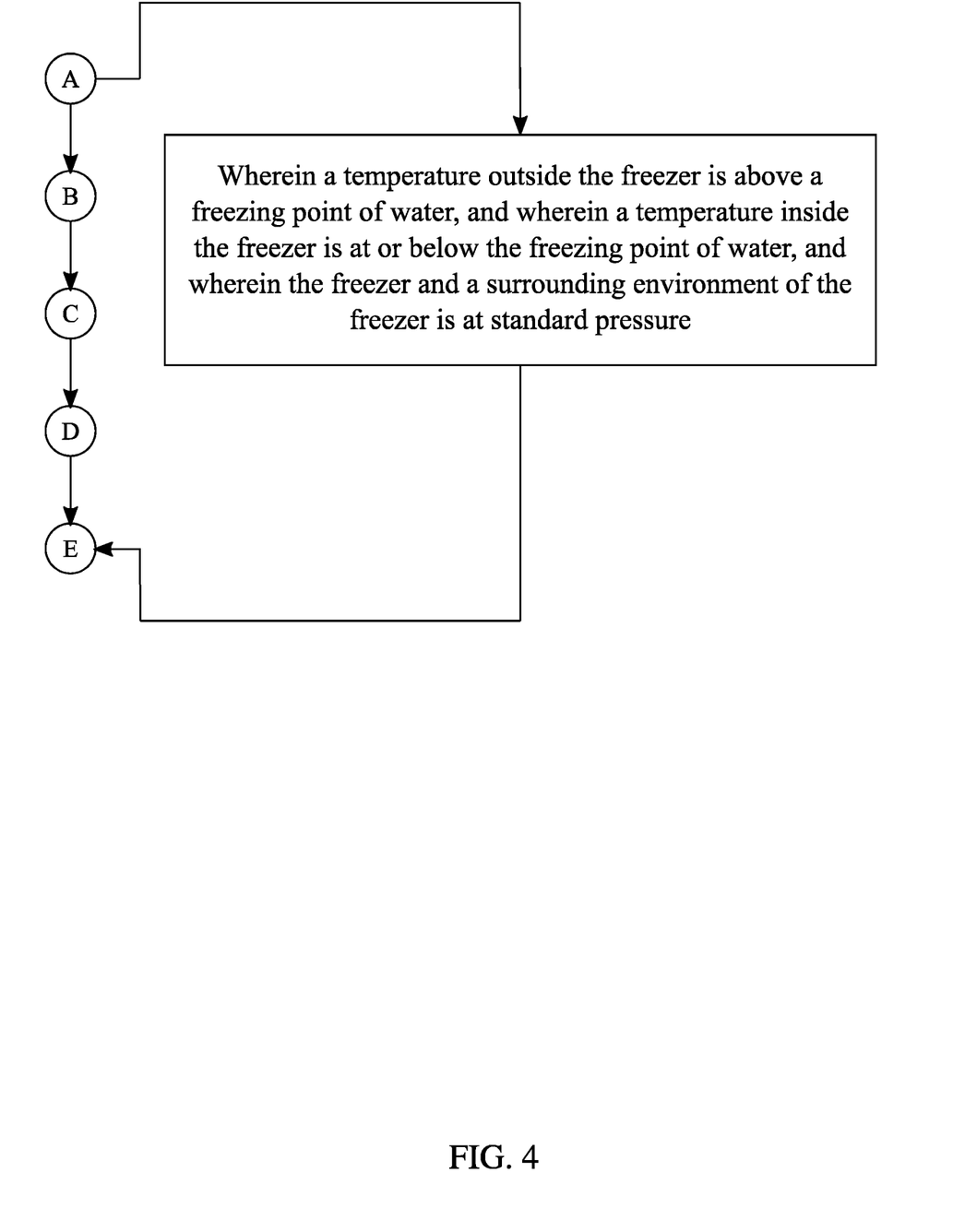
FIG. 4 is a flowchart illustrating the subprocess for freezing a quantity of dosages with a freezer.
Figure 5:
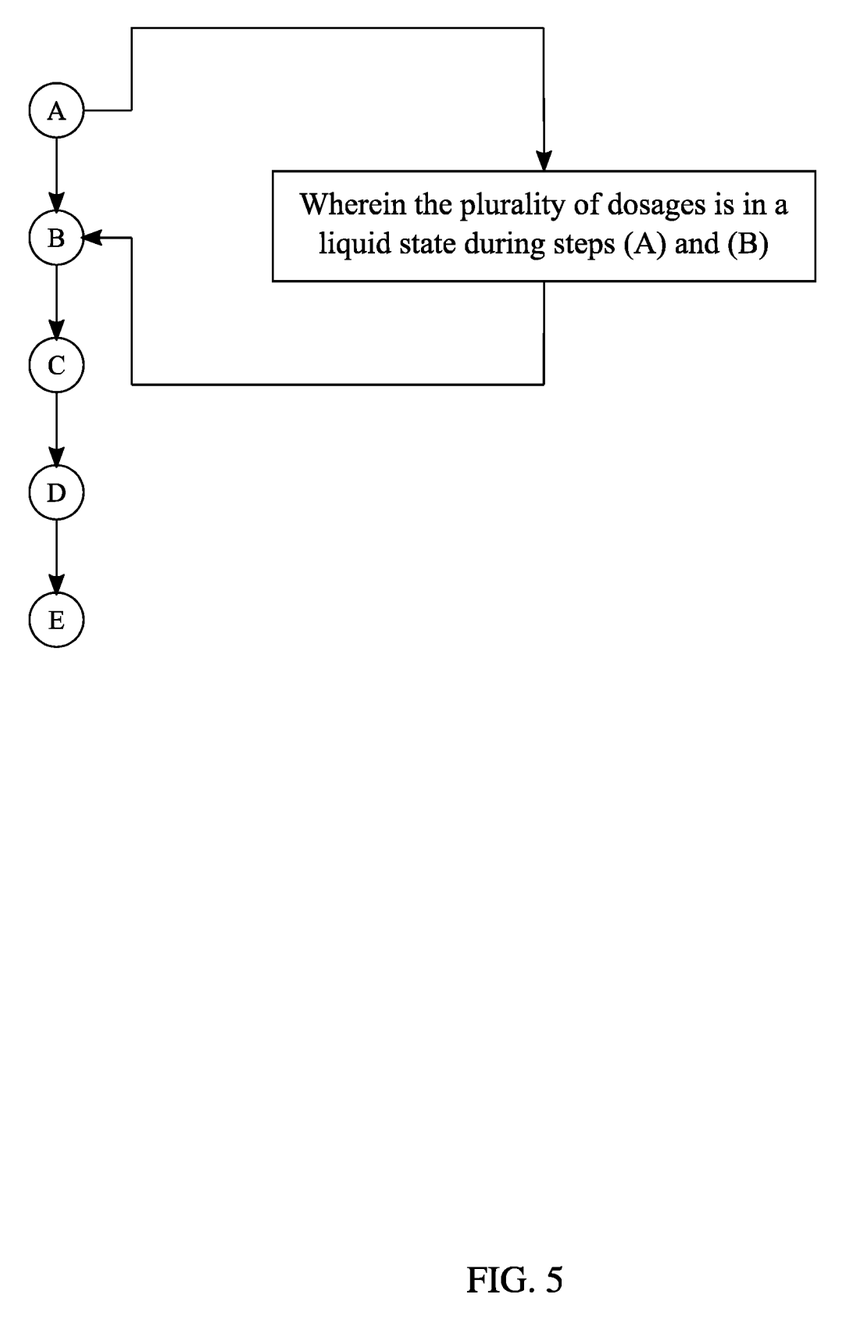
FIG. 5 is a flowchart illustrating the subprocess for placing plurality of dosages within a freezer, while each of the plurality of dosages is liquid.
Figure 6:
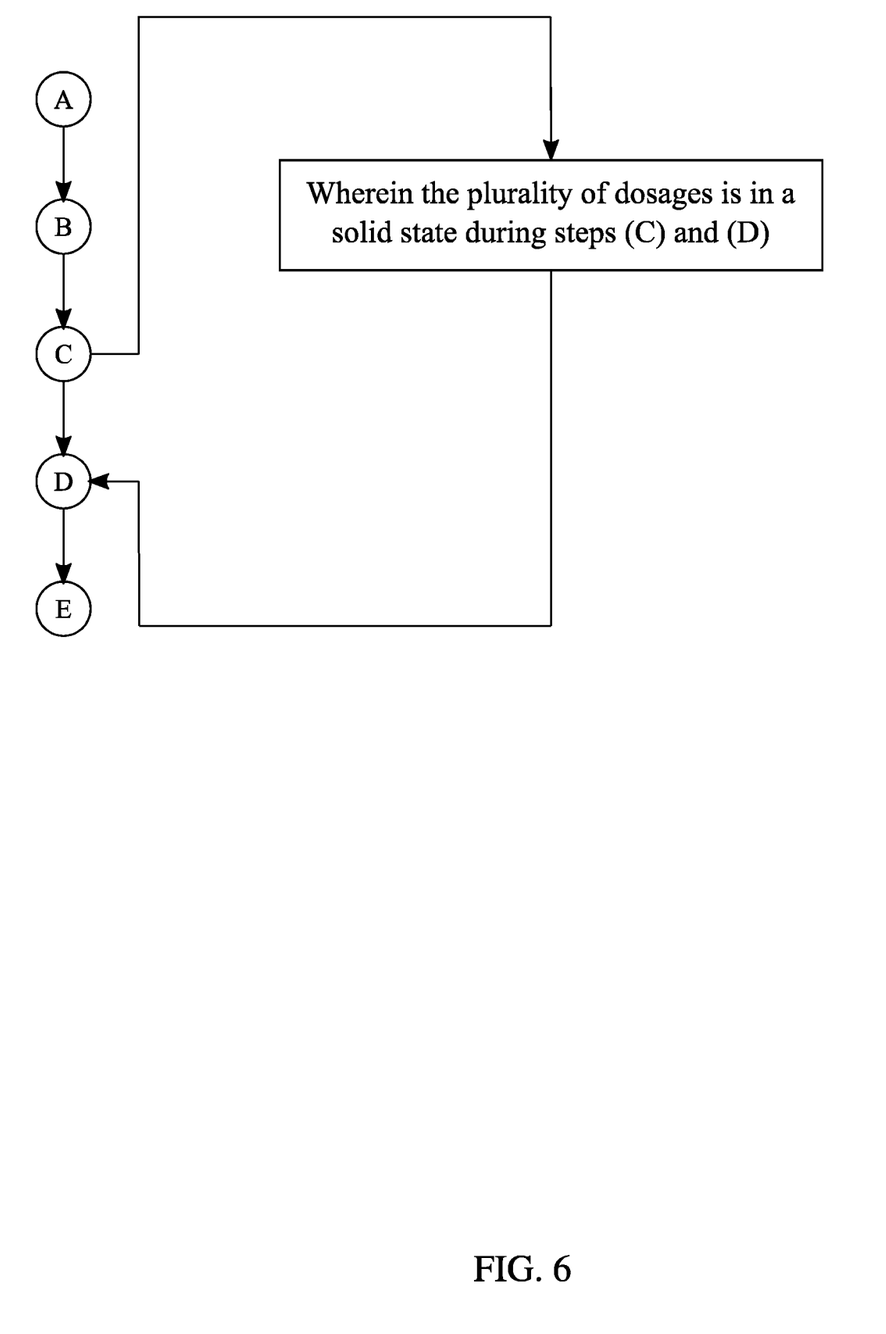
FIG. 6 is a flowchart illustrating the subprocess for placing an arbitrary dosage into a mouth, while each of the plurality of dosages is solid.
Figure 7:
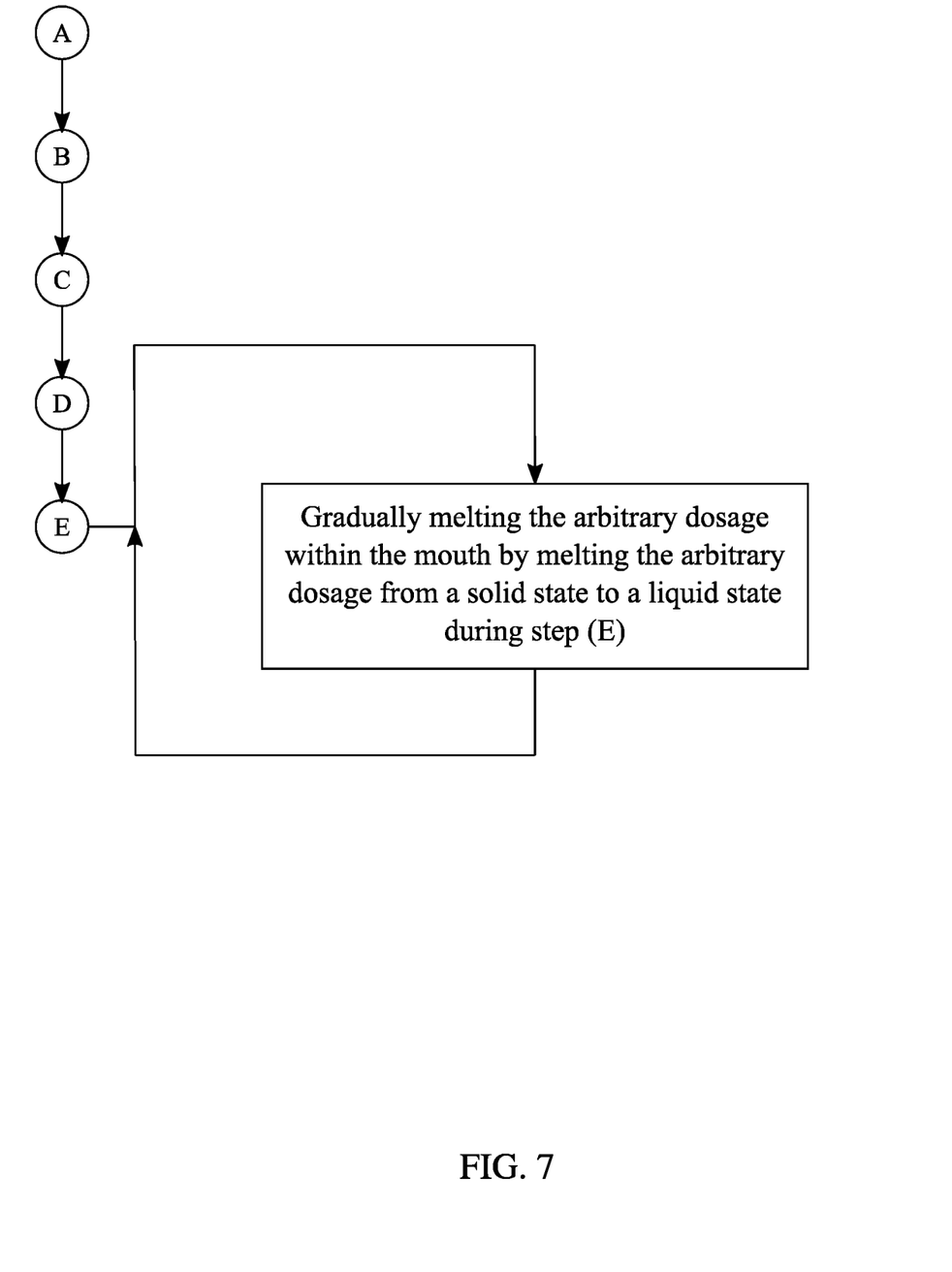
FIG. 7 is a flowchart illustrating the subprocess for melting the arbitrary dosage within the mouth.

As seen in FIG. 4, the plurality of dosages hardens within the freezer as a temperature outside the freezer is above a freezing point of water, and a temperature inside the freezer is at or below the freezing point of water, while the freezer and a surrounding environment of the freezer is at standard pressure. Thus, before the plurality of dosages is placed within the freezer, the plurality of dosages is in a liquid state during Step A and Step B, seen in FIG. 5. The plurality of dosages is in a solid-state during Step C and Step D so that cooling sensations can be directly applied onto the sore throat of a user, seen in FIG. 6. The arbitrary dosage gradually melts within the mouth by melting the arbitrary dosage from the solid-state back into to a liquid state during Step E as the temperature within the mouth of the user is above the freezing point of water, seen in FIG. 7.

Figure 1:
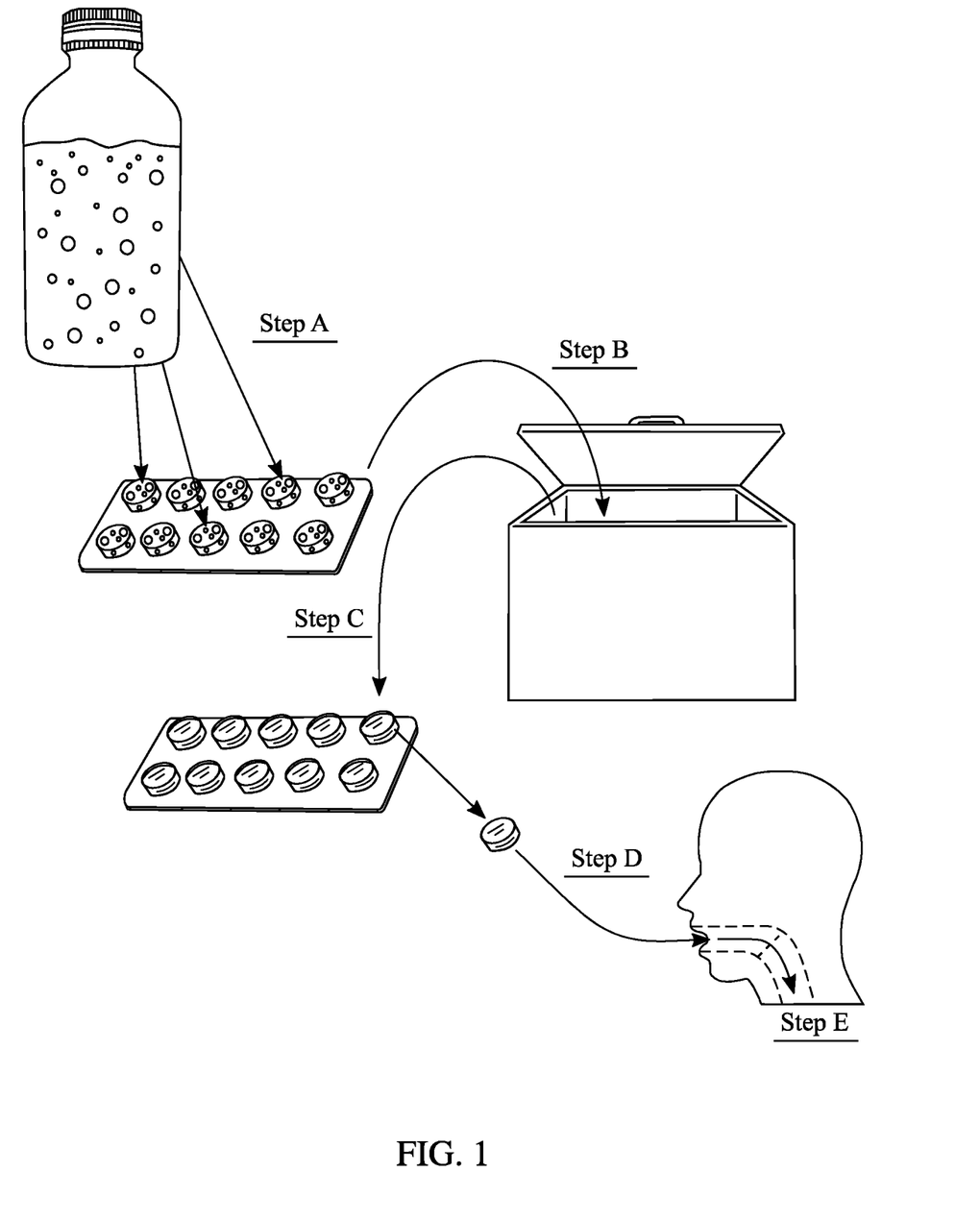
FIG. 1 is a schematic view for a method of the present invention.
Figure 8:
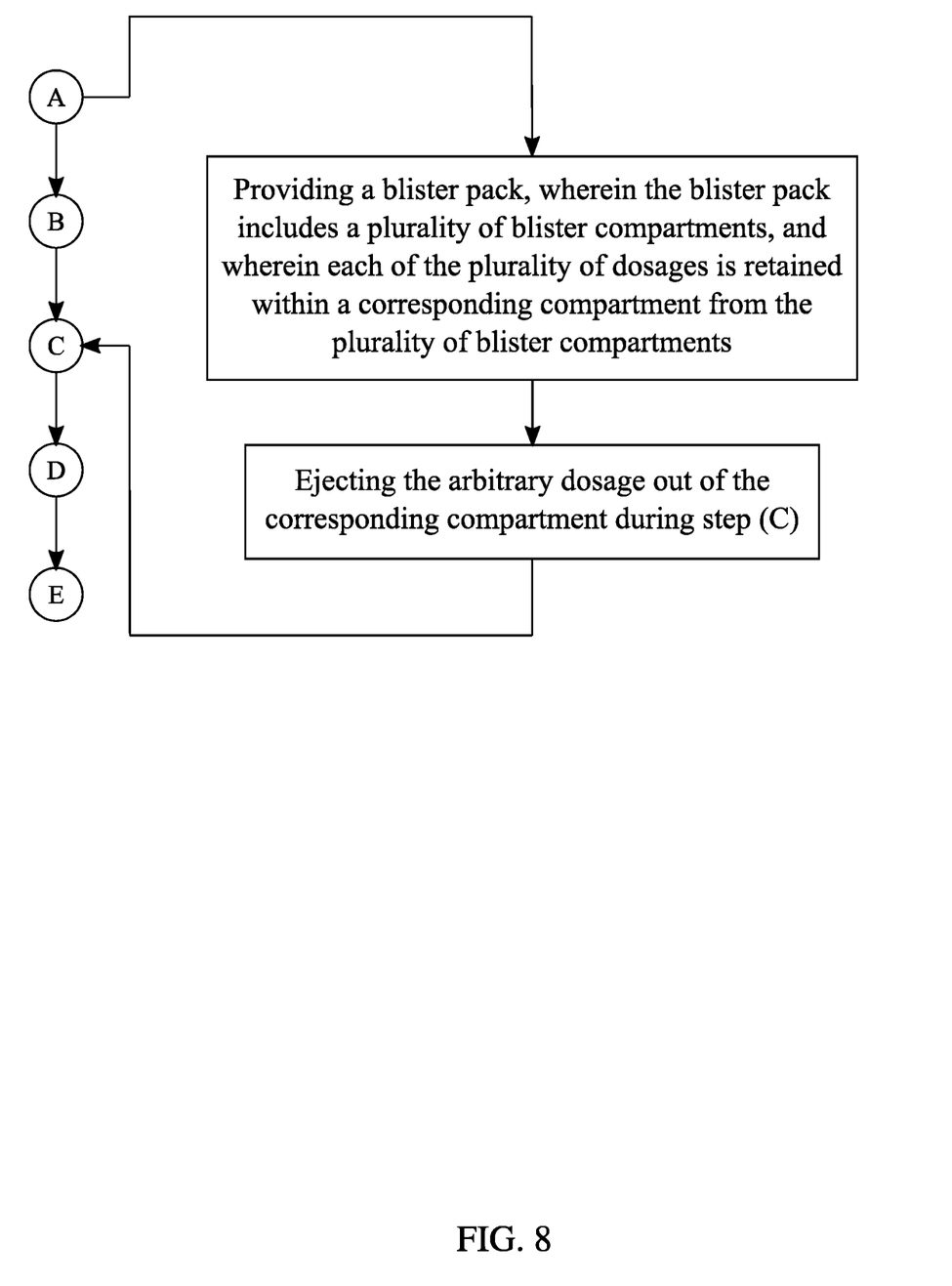
FIG. 8 is a flowchart illustrating the subprocess for removing the arbitrary dosage from a blister pack.

A blister pack is provided in order to safely contain and protect the plurality of dosages especially while in the freezer, seen in FIG. 1 and FIG. 8. The blister pack includes a plurality of blister compartments, and each of the plurality of dosages is retained within a corresponding compartment from the plurality of blister compartments. The plurality of blister compartments contains the plurality of dosages before the plurality of dosages harden within the freezer. The plurality of dosages therefore takes the shape of each of the plurality of blister compartments as the plurality of dosages freezes from Step B to Step C. The plurality of blister compartments is preferably made of a plastic material that allow each of the plurality of dosages to be removed from the corresponding compartment. Moreover, a backing of the blister pack covers each of the plurality of blister compartments and effectively houses each of the plurality of dosages in the corresponding compartment. The backing is preferably made of aluminum foil material that allows a user to easily puncture and access each of the plurality of dosages from the corresponding compartments. The arbitrary dosage is ejected out of the corresponding compartment during Step C in order to individually take each dosage.

Moreover, a storage volume of each of the plurality of blister compartments is greater than or equal to a solid-state volume for each of the plurality of dosages because the volume for each of the plurality of dosages expands as each of plurality of dosages freezes from a liquid state into a solid state. Thus, the storage volume of each of the plurality of blister compartments cannot be sized to only retain a liquid-state volume of each of the plurality of dosages, otherwise each of the plurality of dosages will break out of the corresponding compartment as each of plurality of dosages freezes from a liquid state into a solid state. The storage volume is the internal space of the corresponding compartment occupied by each of the plurality of dosages.

In the preferred embodiment of the present invention, the quantity of medicated solution includes at least one compositional constituent selected from a group consisting of: a quantity of water, a quantity of honey, a quantity of monk fruit extract, a quantity of flavoring, a quantity of coloring, a quantity of stabilizer, a quantity of citric acid, a quantity of malic acid, a quantity of sunflower lecithin, a quantity of sodium citrate, a quantity of ascorbic acid, a quantity of zinc, a quantity of echinacea, a quantity of menthol eucalyptus, and combinations thereof. The quantity of medicated solution effectively coats and has medicinal effects with a sore throat with a combination of compositional constituents from the group. The quantity of water serves as a solvent that combines the combination of compositional constituents from the aforementioned group. The quantity of honey, the quantity of monk fruit extract, the quantity of flavoring, and the quantity of malic acid enhance the taste of each dosage. The quantity of coloring enhances the appearance of each dosage. The quantity of stabilizer serves as a thickening agent and aids with the lubrication of the throat. The quantity of stabilizer is preferably ICE 200. The quantity of citric acid also contributes to the taste of the of each dosage while activating salivation within the mouth of the user. The quantity of sunflower lecithin serves as an emulsifier. The quantity of sodium citrate facilitates the breakdown of mucus. The quantity of ascorbic acid supports the immune system of the user, facilitating the healing process of the sore throat. The quantity of zinc prevents the sore throat symptom from becoming worse. The quantity of echinacea both aids the immune system and relieves the intensity of a sore throat. The quantity of menthol eucalyptus provides a cooling effect with the sore throat, enhancing the numbing effects of the quantity of medication solution.

In the preferred embodiment of the present invention, the combination of compositional constituents is combined in accordance to the following ratio. The quantity of water is approximately 95.82% weight (wt.) of the quantity of medicated solution, wherein the term "approximately" preferably means within an error range of up to ±0.05% wt. The quantity of honey is approximately 0.55% wt. of the quantity of medicated solution, wherein the term "approximately" preferably means within an error range of up to ±0.05% wt. The quantity of monk fruit extract is approximately 0.30% wt. of the quantity of medicated solution, wherein the term "approximately" preferably means within an error range of up to ±0.05% wt. The quantity of flavoring is approximately 0.27% wt. of the quantity of medicated solution, wherein the term "approximately" preferably means within an error range of up to ±0.05% wt. The quantity of coloring is approximately 0.22% wt. of the quantity of medicated solution. The quantity of stabilizer is approximately 0.55% wt. of the quantity of medicated solution, wherein the term "approximately" preferably means within an error range of up to ±0.05% wt. The quantity of sunflower lecithin is approximately 0.49% wt. of the quantity of medicated solution, wherein the term "approximately" preferably means within an error range of up to ±0.05% wt. The quantity of citric acid is approximately 0.47% wt. of the quantity of medicated solution, wherein the term "approximately" preferably means within an error range of up to ±0.05% wt. The quantity of malic acid is approximately 0.47% wt. of the quantity of medicated solution, wherein the term "approximately" preferably means within an error range of up to ±0.05% wt. The quantity of sodium citrate is approximately 0.44% wt. of the quantity of medicated solution, wherein the term "approximately" preferably means within an error range of up to ±0.05% wt. The quantity of ascorbic acid is approximately 0.41% wt. of the quantity of medicated solution, wherein the term "approximately" preferably means within an error range of up to ±0.05% wt. The quantity of zinc is approximately 0.02% wt. of the quantity of medicated solution, wherein the term "approximately" preferably means within an error range of up to ±0.05% wt. The quantity of echinacea is approximately 0.13% wt. of the quantity of medicated solution, wherein the term "approximately" preferably means within an error range of up to ±0.05% wt. The quantity of menthol eucalyptus is approximately 0.27% wt. of the quantity of medicated solution, wherein the term "approximately" preferably means within an error range of up to ±0.05% wt.

The method of manufacturing the quantity of medicated solution begins by blending a quantity of hydrocolloid with quantity of water in order to form a solvent mixture. The quantity of water is preferably warmed. The gum solution is mixed with high sheer. The solvent mixture, the gum solution, the quantity of sunflower lecithin, the quantity of sodium citrate, the quantity of zinc, the quantity of echinacea, and the quantity of menthol eucalyptus are added to a kettle to form a medicated mixture. The medicated mixture is brought to a boil. Once the medicated mixture reaches a temperature of 180 degrees Fahrenheit, the quantity of honey, the quantity of monk fruit extract, the quantity of flavoring, and the quantity of coloring are added to the medicated mixture in the kettle to form a final product. The final product is dispensed into each blister compartment of the blister pack and cooled. Each blister compartment ranges from 4.5 grams to 5.5 grams. In order to cool the final product, the blister pack is stored in a freezer at a preferable temperature ranging from 0 degrees to 10 degrees Fahrenheit.

Although the invention has been explained in relation to its preferred embodiment, it is to be understood that many other possible modifications and variations can be made without departing from the spirit and scope of the invention as hereinafter claimed.

What is claimed is:

1. A method of administering a freezable cough drop to a user, the method comprising the steps of:
   (A) manufacturing a quantity of medicated solution by warming a quantity of water, then blending the quantity of water with a quantity of hydrocolloid in order to form a solvent mixture, then boiling the solvent mixture, a quantity of sunflower lecithin, a quantity of sodium citrate, a quantity of zinc, a quantity of echinacea, and a quantity of menthol eucalyptus within a kettle to form a medicated mixture, and then adding a quantity of honey, a quantity of monk fruit extract, a quantity of flavoring, and a quantity of coloring once the medicated mixture reaches 180 degrees Fahrenheit in order to finally form the quantity of medicated solution, wherein the quantity of medicated solution is an aqueous solution, and wherein the quantity of medicated solution is portioned into a plurality of dosages, and wherein the quantity of water is approximately 95.82% weight (wt.) of the quantity of medicated solution, and wherein the quantity of honey is approximately 0.55% wt. of the quantity of medicated solution, and wherein the quantity of monk fruit extract is approximately 0.30% wt. of the quantity of medicated solution, and wherein the quantity of flavoring is approximately 0.27% wt. of the quantity of medicated solution, and wherein the quantity of coloring is approximately 0.22% wt. of the quantity of medicated solution, and wherein a quantity of stabilizer as the quantity of hydrocolloid is approximately 0.14% wt. of the quantity of medicated solution, and wherein a quantity of citric acid is approximately 0.47% wt. of the quantity of medicated solution, and wherein the quantity of citric acid is configured to activate salivation within a mouth of the user, and wherein a quantity of malic acid is approximately 0.47% wt. of the quantity of medicated solution, and wherein the quantity of malic acid is configured to enhance a taste of each dosage, and wherein the quantity of sunflower lecithin is approximately 0.49% wt. of the quantity of medicated solution, and wherein the quantity of sodium citrate is approximately 0.44% wt. of the quantity of medicated solution, and wherein a quantity of ascorbic acid is approximately 0.41% wt. of the quantity of medicated solution, and wherein the quantity of ascorbic acid is configured to heal a sore throat of the user, and wherein the quantity of zinc is approximately 0.02% wt. of the quantity of medicated solution, and wherein the quantity of echinacea is approximately 0.13% wt. of the quantity of medicated solution, and wherein the quantity of echinacea is sourced as an extract, and wherein the quantity of menthol eucalyptus is approximately 0.27% wt. of the quantity of medicated solution, and wherein the quantity of menthol eucalyptus is sourced as a menthol-infused eucalyptus oil;

(B) placing the plurality of dosages within a freezer for a specified time period;

(C) removing at least one arbitrary dosage from the freezer, wherein the arbitrary dosage is any one of the plurality of dosages;

(D) placing the arbitrary dosage within the mouth of the user; and, (E) dispensing the arbitrary dosage from the mouth into a sore throat of the user by gradually dissolving the arbitrary dosage within the mouth.

2. The method of administering a freezable cough drop to a user, the method as claimed in claim 1, wherein steps (A) through (E) are executed in sequence.

3. The method of administering a freezable cough drop to a user, the method as claimed in claim 1, wherein the specified time period is 12 hours.

4. The method of administering a freezable cough drop to a user, the method as claimed in claim 1, wherein a temperature outside the freezer is above a freezing point of water, and wherein a temperature inside the freezer is at or below the freezing point of water, and wherein the freezer and a surrounding environment of the freezer is at standard pressure.

5. The method of administering a freezable cough drop to a user, the method as claimed in claim 1, wherein the plurality of dosages is in a liquid state during steps (A) and (B).

6. The method of administering a freezable cough drop to a user, the method as claimed in claim 1, wherein the plurality of dosages is in a solid state during steps (C) and (D).

7. The method of administering a freezable cough drop to a user, the method as claimed in claim 1 comprising the step of:

gradually melting the arbitrary dosage within the mouth by melting the arbitrary dosage from a solid state to a liquid state during step (E).

8. The method of administering a freezable cough drop to a user, the method as claimed in claim 1 comprising the steps of:

providing a blister pack, wherein the blister pack includes a plurality of blister compartments, and wherein each of the plurality of dosages is retained within a corresponding compartment from the plurality of blister compartments; and, ejecting the arbitrary dosage out of the corresponding compartment during step (C).

9. The method of administering a freezable cough drop to a user, the method as claimed in claim 8, wherein a storage volume of each of the plurality of blister compartments is greater than or equal to a solid-state volume for each of the plurality of dosages.

* * * * *